United States Patent
Perfitt et al.

(10) Patent No.: US 9,180,076 B2
(45) Date of Patent: Nov. 10, 2015

(54) HAIR COLOURING COMPOSITION

(71) Applicant: Herb UK Limited, Lymington (GB)

(72) Inventors: Raoul John Perfitt, Lymington (GB); Cicely Andrea Ruth Carimbocas, Lymington (GB)

(73) Assignee: Herb UK Limited, Lymington (GB)

( * ) Notice: Subject to any disclaimer, the term of this patent is extended or adjusted under 35 U.S.C. 154(b) by 0 days.

(21) Appl. No.: 14/472,726

(22) Filed: Aug. 29, 2014

(65) Prior Publication Data

US 2015/0174022 A1 Jun. 25, 2015

(30) Foreign Application Priority Data

Dec. 19, 2013 (GB) .................................. 1322578.4

(51) Int. Cl.

| | | |
|---|---|---|
| *A61Q 5/10* | (2006.01) | |
| *A61K 8/42* | (2006.01) | |
| *A61K 8/34* | (2006.01) | |
| *A61K 8/36* | (2006.01) | |
| *A61K 8/37* | (2006.01) | |
| *A61K 8/45* | (2006.01) | |
| *A61Q 5/06* | (2006.01) | |
| *A61K 8/22* | (2006.01) | |
| *A61K 8/41* | (2006.01) | |

(52) U.S. Cl.
CPC ... *A61K 8/42* (2013.01); *A61K 8/22* (2013.01); *A61K 8/34* (2013.01); *A61K 8/361* (2013.01); *A61K 8/37* (2013.01); *A61K 8/41* (2013.01); *A61K 8/45* (2013.01); *A61Q 5/06* (2013.01); *A61Q 5/10* (2013.01)

(58) Field of Classification Search
CPC ............. A61Q 5/10; A61K 8/34; A61K 8/41; A61K 8/361; A61K 8/42
USPC ............................................................ 8/405
See application file for complete search history.

(56) References Cited

U.S. PATENT DOCUMENTS

| | | | | |
|---|---|---|---|---|
| 7,041,142 | B2 * | 5/2006 | Chan et al. ........................ | 8/405 |
| 8,382,854 | B2 | 2/2013 | Schmenger et al. | |
| 2003/0233714 | A1 * | 12/2003 | Hammond et al. ............... | 8/405 |
| 2004/0226109 | A1 | 11/2004 | Cotteret et al. | |
| 2005/0125912 | A1 | 6/2005 | Desenne et al. | |
| 2012/0317734 | A1 * | 12/2012 | Martinez-Santiago et al. .. | 8/416 |

FOREIGN PATENT DOCUMENTS

| | | |
|---|---|---|
| DE | 19701422 | 3/1998 |
| EP | 1340489 | 9/2003 |
| EP | 1420752 | 2/2012 |
| WO | WO03017957 | 3/2003 |
| WO | WO 2008063501 | 5/2008 |

OTHER PUBLICATIONS

AMIDET® N product brochure, Kao Chemicals, available on internet, Jul. 2013.
Hair Coloration (Personal care) presentation, Kao Chemicals, available on internet, Jul. 2013.
Search Report issued in GB1322578.4, Jul. 4, 2014.
International Search Report and Written Opinion issued in PCT/GB2014/053424, Feb. 3, 2015.
Database GNPD [Online], Mintel, Naked Earth: "Permanent hair Colour", XP002734882, Database accession No. 744480, Jul. 2007.
Database GNPD [Online], Mintel, Modi-Revlon: "Hair Colour", XP002734883, Database accession No. 1962852, Jan. 2013.
Database GNPD [Online], Mintel, Revlon: "Permanent Beautiful Color", XP002734884, Database accession No. 1181593, Sep. 2009.

* cited by examiner

*Primary Examiner* — Eisa Elhilo
(74) *Attorney, Agent, or Firm* — Bell & Manning, LLC

(57) ABSTRACT

A hair coloring composition comprises an N-PEG amide of a fatty acid and an N-ethoxylated alkyl amine. Also provided are a kit comprising the hair coloring composition and an activator, and an activated hair coloring composition obtainable by mixing the hair coloring composition in a 1:1 ratio by weight with an activator comprising from 2% to 15% by weight hydrogen peroxide.

20 Claims, No Drawings

HAIR COLOURING COMPOSITION

The present application claims priority to GB Patent Application No. 1322578.4 that was filed Dec. 19, 2013, the entire contents of which is hereby incorporated by reference.

The present invention relates to a hair colouring composition.

Hair colouring compositions are well known for use in changing the colour of an individual's hair, such as human head hair. This may be to restore the original colour lost as a result of natural aging, through bleaching, or following a previous use of a hair colouring composition. Alternatively, hair colouring compositions may be used to change the current hair colour for a new colour, for fashion or other reasons.

Traditionally, hair colouring compositions are categorised according to the permanence of the effect achieved. Thus, temporary hair colours simply apply a colour to the exterior of the hair, which is removed on washing. Semi-permanent hair colours typically survive for 6 to 12 washes. Demi-permanent hair colours typically survive for 20 to 28 washes. Permanent hair colours do not wash out; however, growth of the hair reveals a section of un-dyed hair near the root, which will eventually grow out to replace the coloured hair.

The different degrees of permanence of the hair colour reflects differences in the mechanism by which the dye operates. In order to survive washing, the molecules responsible for the change in colour must penetrate into the interior of the hair strand. This is promoted by the use of smaller molecules and/or by the use of an alkalizing agent to raise the pH and open cuticles in the hair strand (as in demi-permanent and permanent hair colours).

Demi-permanent and permanent hair dyes typically use an oxidative dye together with an oxidizing agent, commonly hydrogen peroxide. The oxidizing agent has two effects: it causes partial or total bleaching of any existing hair colour (also known as 'lift'), enabling the replacement hair colour to be seen more clearly, and it enables a chemical reaction of the oxidative dye. This chemical reaction is responsible for converting some or all of the dye into the form in which it provides the required coloration, and also increases the size of the dye molecules, thereby restricting the ability of the dye to exit the hair strand on washing. The hair colouring composition is therefore typically mixed with an activator, comprising the oxidizing agent, immediately before application to the hair.

The alkalizing agent used to raise the pH of the colouring composition also varies according to the desired effect. Ammonia is considered to be particularly effective at opening cuticles in the hair strand, and is typically used for permanent hair colours. However, this same effectiveness can result in the hair becoming dry and brittle. Ammonia also allows much of the existing, natural hair colour to be removed, which can lead to a flat, unnatural appearance when the artificial colour is applied. Thus, demi-permanent hair colours typically use a non-ammonia alkalizing agent, such as ethanolamine.

Hair colouring compositions must be formulated so that the composition evenly coats the hair strands and remains on the hair strands whilst the colouring process takes effect. Thus, hair colouring compositions are typically formulated as creams, mousses or gels. Furthermore, the relatively harsh chemical reagents necessary to achieve hair coloration can cause irritation or allergy. The hair colouring composition may therefore also contain ingredients intended to mitigate these effects.

There are concerns regarding the health risks of hair colouring compositions. In addition to damage to the hair and scalp itself, some ingredients of the hair colouring composition may pose longer term health risks. In particular, there is concern that some common ingredients have or can give rise to sensitivity. In addition to the effect on the recipient of the hair colouring, it is also necessary to consider the health risks provided to hair care professionals who are applying the products to customers, and to the wider public at large if the products find their way into the environment.

There is therefore a need for hair colouring compositions which have low environmental impact and reduced health risks. The present invention has been conceived with these issues in mind.

The invention provides a hair colouring composition comprising an N-PEG amide of a fatty acid and an N-ethoxylated alkyl amine.

The invention also provides a kit comprising the hair colouring composition of the invention together with an activator comprising hydrogen peroxide.

Further, the invention provides an activated hair colouring composition obtainable by mixing the hair colouring composition of the invention in a 1:1 ratio by weight with an activator comprising hydrogen peroxide.

Preferably the hair colouring composition is a permanent hair colouring composition.

The hair colouring composition of the present invention comprises an N-PEG amide of a fatty acid. Preferably, the N-PEG amide of a fatty acid is an N-PEG rapeseedamide, for example PEG-4 rapeseedamide.

PEG-4 rapeseedamide is a known ingredient for use in cosmetic products, and is sold by Kao Chemicals GmbH of Emmerich, Germany, under the trade name AMIDET® N. PEG-4 rapeseedamide is derived from rapeseed oil $C_{18}$ unsaturated fatty acid, and has good aerobic and anaerobic biodegradability. The present inventors have surprisingly found that PEG-4 rapeseedamide is particularly effective at thickening hair colouring compositions, such as non-ammonia, relatively low pH, oil-based permanent hair colours. Such compositions are relatively difficult to thicken, previously requiring significant quantities of thickening agent. Thus, the use of an N-PEG amide of a fatty acid, such as PEG-4 rapeseedamide, enables a hair colouring composition to be provided having the required characteristics without the need for large quantities of thickener.

In addition, N-PEG amides of fatty acids, such as PEG-4 rapeseedamide, provide good environmental benefits. Unlike other N-ethoxylated fatty acid amides, such as cocamide DEA, N-PEG amides of fatty acids, and particularly PEG-4 rapeseedamide, do not typically contain nitroso amine impurities. Such impurities are associated with health concerns. Furthermore, PEG-4 rapeseedamide is biodegradeable and has low aquatic toxicity.

The amount of the N-PEG amide of a fatty acid present in the hair colouring composition may be 5% or more, 10% or more, 11% or more, 12% or more, 13% or more, 14% or more, 15% or more, 16% or more, 17% or more, or 18% or more, by weight based on the total weight of the composition. Alternatively or additionally, the amount of the N-PEG amide of the a fatty acid present in the hair colouring composition may be 30% or less, 25% or less, 24% or less, 23% or less, 22% or less, 21% or less, 20% or less, 19% or less, or 18% or less, by weight based on the total weight of the composition. Any endpoint may be combined with any other endpoint to define a suitable range; thus, for example, the N-PEG amide may be present in an amount of from 15% to 25% by weight, or from 17% to 22% by weight, based on the total weight of the composition.

The hair colouring composition of the invention further comprises an N-ethoxylated alkyl amine. The N-ethoxylated alkyl amine acts as a surfactant. Preferably, the N-ethoxylated alkyl amine is an N-PEG alkyl amine and/or an N-ethoxylated soyamine. More preferably, the N-ethoxylated alkyl amine is selected from PEG-2 soyamine and PEG-2 oleamine. The present inventors have found that the combination of an N-PEG amide of a fatty acid, such as PEG-4 rapeseedamide, with an N-ethoxylated alkyl amine, such as PEG-2 soyamine or PEG-2 oleamine, is particularly effective in enabling the production of a non-ammonia, relatively low pH, oil-based permanent hair colour.

The amount of N-ethoxylated alkyl amine present in the hair colouring composition may be 10% or more, 15% or more, 20% or more, 21% or more, 22% or more, 23% or more, 24% or more, 25% or more, or 26% or more, by weight based on the total weight of the composition. Alternatively or additionally, the amount of N-ethoxylated alkyl amine present in the hair colouring composition may be 40% or less, 35% or less, 34% or less, 33% or less, 32% or less, 31% or less, 30% or less, 29% or less, 28% or less, 27% or less, or 26% or less, by weight based on the total weight of the composition. Any endpoint may be combined with any other endpoint to define a suitable range; thus, for example, the N-ethoxylated alkyl amine may be present in an amount of from 20% to 30% by weight, or from 22% to 28% by weight, based on the total weight of the composition.

The hair colouring composition may further comprise one or more alcohols selected from ethanol, ethanediols, propanol, propanediols, and propanetriols. Preferably, the hair colouring composition comprises at least one of ethanol and propanediol. More preferably, the hair colouring composition comprises ethanol and propanediol. The propanediol may be 1,2-propanediol or 1,3-propanediol, but is preferably 1,3-propanediol.

The inventors have found that the use of alcohol assists in solubilising the ingredients of the hair colouring composition.

The total amount of the one or more alcohols present in the hair colouring composition may be 5% or more, 10% or more, 11% or more, 12% or more, 13% or more, 14% or more, 15% or more, 16% or more, 17% or more, or 18% or more, by weight based on the total weight of the composition. Alternatively or additionally, the total amount of the one or more alcohols present in the hair colouring composition may be 30% or less, 25% or less, 24% or less, 23% or less, 22% or less, 21% or less, 20% or less, 19% or less, or 18% or less, by weight based on the total weight of the composition. Any endpoint may be combined with any other endpoint to define a suitable range; thus, for example, the one or more alcohols may be present in a total amount of from 15% to 25% by weight, or from 17% to 22% by weight, based on the total weight of the composition.

The hair colouring composition may comprise 5% or more, 6% or more, 7% or more, 8% or more, 9% or more, or 10% or more by weight ethanol, based on the total weight of the composition. Alternatively or additionally, the hair colouring composition may comprise 15% or less, 14% or less, 13% or less, 12% or less, 11% or less, or 10% or less by weight ethanol, based on the total weight of the composition. Any endpoint may be combined with any other endpoint to define a suitable range; thus, for example, ethanol may be present in a total amount of from 5% to 15% by weight, or from 8% to 11% by weight, based on the total weight of the composition The hair colouring composition may comprise 4% or more, 5% or more, 6% or more, 7% or more, or 8% or more by weight propanediol, based on the total weight of the composition. Alternatively or additionally, the hair colouring composition may comprise 12% or less, 11% or less, 10% or less, 9% or less, or 8% or less by weight propanediol, based on the total weight of the composition. Any endpoint may be combined with any other endpoint to define a suitable range; thus, for example, propanediol may be present in a total amount of from 5% to 15% by weight, or from 8% to 11% by weight, based on the total weight of the composition.

The hair colouring composition may further comprise a fatty acid. The fatty acid may have 14 or more, 16 or more, or 18 or more carbon atoms. Alternatively or additionally, the fatty acid may have 22 or fewer, 20 or fewer, or 18 or fewer carbon atoms. Any endpoint may be combined with any other endpoint to define a suitable range. Thus, for example, the fatty acid may have from 14 to 22 carbon atoms.

The fatty acid may be saturated or unsaturated. Preferably, the fatty acid has a single double bond. Preferably, the fatty acid has 18 carbon atoms. More preferably, the fatty acid is oleic acid.

The fatty acid may be present in an amount of 1% or more, 2% or more, 3% or more, or 4% or more, by weight based on the total weight of the composition. Alternatively or additionally, the fatty acid may be present in an amount of 7% or less, 6% or less, 5% or less or 4% or less, by weight based on the total weight of the composition. Any endpoint may be combined with any other endpoint to define a suitable range; thus, for example, the fatty acid may be present in a total amount of from 2% to 6% by weight, or from 3% to 5% by weight, based on the total weight of the composition.

The hair colouring composition may further comprise a non-ammonia alkalizing agent selected from the group consisting of monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3 propanediol, and mixtures thereof. Preferably, the non-ammonia alkalizing agent is monoethanolamine or triethanolamine. More preferably, the non-ammonia alkalizing agent is monoethanolamine.

The non-ammonia alkalizing agent may be present in an amount of 1% or more, 2% or more, 3% or more, or 4% or more, by weight based on the total weight of the composition. Alternatively or additionally, the non-ammonia alkalizing agent may be present in an amount of 7% or less, 6% or less, 5% or less or 4% or less, by weight based on the total weight of the composition. Any endpoint may be combined with any other endpoint to define a suitable range; thus, for example, the non-ammonia alkalizing agent may be present in a total amount of from 2% to 6% by weight, or from 3% to 5% by weight, based on the total weight of the composition.

Preferably, the hair colouring composition comprises 1% or less by weight of ammonia. More preferably, the hair colouring composition comprises 0.9% or less, 0.8% or less, 0.7% or less, 0.6% or less, 0.5% or less, 0.4% or less, 0.3% or less, 0.2% or less, 0.1% or less, 0.05% or less, 0.01% or less, 0.005% or less, or 0.001% or less by weight of ammonia. More preferably, the hair colouring composition is at least substantially free from ammonia.

Preferably, the hair colouring composition comprises PEG-4 rapeseedamide, PEG-2 soyamine and/or PEG-2 oleamine, ethanol, propanediol, oleic acid and ethanolamine (monoethanolamine or triethanolamine). More preferably, the hair colouring composition comprises these ingredients in the following proportions, based on the total weight of the composition:

| | |
|---|---|
| PEG-4 rapeseedamide | 14 to 22% by weight |
| PEG-2 soyamine and/or PEG-2 oleamine | 20 to 32% by weight |
| Ethanol | 8 to 12% by weight |
| Propanediol | 6 to 10% by weight |
| Oleic acid | 3 to 5% by weight |
| Ethanolamine | 2 to 8% by weight |

The hair colouring composition will typically comprise further ingredients, including one or more dye compounds. Exemplary further ingredients include a chelating agent, botanical elements, and emollients/humectants. A chelating agent, such as for example tetrasodium EDTA, ensures effective colour deposition and retards oxidation of the product. Botanical elements may act as antioxidants (for example grapefruit/orange extracts) and/or soothing/conditioning agents (for example comfrey leaf extract). Emollients/humectants (for example naturally-based examples such as wheat protein and PEG-7 glyceryl cocoate) give shine/gloss to hair.

The hair colouring composition of the invention will typically require activation with an oxidizing activator during use. Typically, a suitable activator comprises hydrogen peroxide. Thus, a further aspect of the invention provides a kit comprising a hair colouring composition of the invention together with an activator comprising hydrogen peroxide.

The amount of hydrogen peroxide present in the activator may be 2% or more, 2.5% or more, 3% or more, 4% or more, 5% or more, 6% or more, 7% or more, 8% or more, 9% or more, 10% or more, 11% or more, or 12% or more, based on the total weight of the activator. Alternatively or additionally, the amount of hydrogen peroxide present in the activator may be 15% or less, 12% or less, 11% or less, 10% or less, 9% or less, 8% or less, 7% or less, 6% or less, 5% or less, 4% or less, or 3% or less, based on the total weight of the activator. Any endpoint may be combined with any other endpoint to define a suitable range; thus, for example, the hydrogen peroxide may be present in an amount of from 3% to 12% by weight, or from 6% to 9% by weight, based on the total weight of the activator.

The activator is typically mixed with the hair colouring composition immediately before application to the hair.

The activator may be an aqueous liquid activator, or a cream activator.

The cream activator may further comprise a fatty alcohol. The fatty alcohol may have 12 or more, 14 or more, or 16 or more carbon atoms. Alternatively or additionally, the fatty alcohol may have 20 or fewer, 18 or fewer, or 16 or fewer carbon atoms. Any endpoint may be combined with any other endpoint to define a suitable range. Thus, for example, the fatty alcohol may have from 12 to 20 carbon atoms. Preferably, the fatty alcohol has 16 carbon atoms.

The fatty alcohol may be saturated or unsaturated. Preferably the fatty alcohol is saturated. More preferably the fatty alcohol is cetyl alcohol.

The fatty alcohol may be present in an amount of 1.0% or more, 1.5% or more, 2.0% or more, 2.5% or more, or 3.0% or more, by weight based on the total weight of the activator. Alternatively or additionally, the fatty alcohol may be present in an amount of 5.0% or less, 4.5% or less, 4.0% or less, 3.5% or less, or 3.0% or less, by weight based on the total weight of the activator. Any endpoint may be combined with any other endpoint to define a suitable range. Thus, for example, the fatty alcohol may be present in an amount of from 3.0 to 3.5% by weight, based on the total weight of the activator.

A further aspect of the invention provides an activated hair colouring composition obtainable by mixing the hair colouring composition of the invention with an activator as described above, in a 1:1 ratio by weight.

The invention is illustrated by the following Example:

EXAMPLE

A hair colouring composition is prepared by mixing the following components in the proportions (by weight) indicated:

| | |
|---|---|
| PEG-2 soyamine | 26.00 |
| Aqua | 22.25 |
| PEG-4 rapeseedamide | 18.00 |
| Alcohol denatured (ethanol) | 10.00 |
| Propanediol | 8.00 |
| Oleic acid | 4.00 |
| Ethanolamine | 4.00 |
| Parfum | 1.20 |
| Emollient | 1.15 |
| Antioxidants | 0.90 |
| Botanical elements | 0.61 |
| Tetrasodium EDTA | 0.20 |
| Colouring agents and couplers | 3.696 |

For use, an activated hair colouring composition is prepared by mixing the above hair colouring composition in a ratio of 1:1 by weight with an activator comprising 5.4% hydrogen peroxide in an aqueous solution.

Hair samples were dyed using the activated hair colouring composition, and assessed for fading over a 6 week period. The hair samples were washed regularly and found to provide permanent hair colouring. Fading under UV light was within acceptable limits. Coverage of grey hair was good.

Comparative Examples

Comparative formulations were produced in which the PEG-4 rapeseedamide was replaced by (i) cocamide MEA; (ii) PPG-2 hydroxyethyl cocamide; or (iii) Antil HS-60 (a mix of cocamido propyl betaine and glyceryl laurate). Formulation (i) produced a cloudy liquid rather than the required clear liquid. Formulation (iii) did not adequately thicken. Formulation (ii) was also more difficult to thicken than the exemplary formulation above, requiring an increased amount of thickener.

The invention claimed is:

1. A hair colouring composition comprising:
    from 15% to 25% by weight of an N-PEG amide of a fatty acid;
    from 20% to 30% by weight of an N-ethoxylated alkyl amine; and
    from 15% to 25% by weight, in total, of one or more alcohols selected from ethanol, ethanediols, propanol, propanediols, and propanetriols.

2. A hair colouring composition according to claim 1, wherein the N-PEG amide of a fatty acid comprises an N-PEG rapeseedamide.

3. A hair colouring composition according to claim 1, wherein the N-PEG amide of a fatty acid comprises PEG-4 rapeseedamide.

4. A hair colouring composition according to claim 1, wherein the N-ethoxylated alkyl amine comprises at least one of PEG-2 soyamine and PEG-2 oleamine.

5. A hair colouring composition according to claim 1, wherein the one or more alcohols comprise ethanol and propanediol.

6. A hair colouring composition according to claim 1, further comprising a fatty acid.

7. A hair colouring composition according to claim 6, wherein the fatty acid comprises oleic acid.

8. A hair colouring composition according to claim 1, further comprising a non-ammonia alkalizing agent.

9. A hair colouring composition according to claim 8, wherein the non-ammonia alkalizing agent comprises at least one of monoethanolamine and triethanolamine.

10. A hair colouring composition according to claim 1, comprising less than 0.1% by weight ammonia.

11. A kit comprising a hair colouring composition according to claim 1, and an activator.

12. A kit according to claim 11, wherein the activator comprises from 2% to 15% by weight hydrogen peroxide.

13. An activated hair colouring composition obtainable by mixing a hair colouring composition according to claim 1 in a 1:1 ratio by weight with an activator comprising from 2% to 15% by weight hydrogen peroxide.

14. A hair colouring composition comprising:
   from 15% to 25% by weight of PEG-4 rapeseedamide;
   from 20% to 30% by weight, in total, of an N-ethoxylated alkyl amine selected from PEG-2 soyamine, PEG-2 oleamine, and combinations thereof; and
   from 15% to 25% by weight, in total, of one or more alcohols selected from ethanol, ethanediols, propanol, propanediols, and propanetriols.

15. A hair colouring composition according to claim 14, wherein the one or more alcohols are a combination of ethanol and propanediol.

16. A hair colouring composition according to claim 15, further comprising a fatty acid and a non-ammonia alkalizing agent, wherein the fatty acid is oleic acid and the non-ammonia alkalizing agent is selected from monoethanolamine, triethanolamine, and a combination thereof.

17. A hair colouring composition according to claim 16, further wherein the hair colouring composition is substantially free from ammonia.

18. A hair colouring composition consisting of:
   from 15% to 25% by weight of an N-PEG amide of a fatty acid;
   from 20% to 30% by weight, in total, of an N-ethoxylated alkyl amine or a combination of N-ethoxylated alkyl amines;
   from 15% to 25% by weight, in total, of one or more alcohols selected from ethanol, ethanediols, propanol, propanediols, and propanetriols; and
   optionally, one or more of a fatty acid, a non-ammonia alkalizing agent, a parfum, an emollient, an antioxidant, a botanical element, a chelating agent, a humectant, a colouring agent, and a coupler.

19. A hair colouring composition according to claim 18, wherein the N-PEG amide of a fatty acid is PEG-4 rapeseedamide and the N-ethoxylated alkyl amine is PEG-2 soyamine, PEG-2 oleamine, or a combination thereof.

20. A hair colouring composition according to claim 19, further wherein the one or more alcohols are a combination of ethanol and propanediol, further wherein the fatty acid and the non-ammonia alkalizing agent are present in the hair colouring composition, and further wherein the fatty acid is oleic acid and the non-ammonia alkalizing agent is selected from monoethanolamine, triethanolamine, and a combination thereof.

* * * * *